(12) United States Patent
Herskovic (10) Patent No.: US 11,771,919 B2
(45) Date of Patent: Oct. 3, 2023

(54) HYPERTHERMIA BRACHYTHERAPY DEVICE AND METHOD FOR TREATING TUMORS

(71) Applicant: Arnold M. Herskovic, Chicago, IL (US)

(72) Inventor: Arnold M. Herskovic, Chicago, IL (US)

(73) Assignee: Arnold Herskovic, Chicago, IL (US)

( * ) Notice: Subject to any disclaimer, the term of this patent is extended or adjusted under 35 U.S.C. 154(b) by 0 days.

(21) Appl. No.: 17/941,985

(22) Filed: Sep. 9, 2022

(65) Prior Publication Data

US 2023/0093173 A1   Mar. 23, 2023

Related U.S. Application Data (60) Provisional application No. 63/243,092, filed on Sep. 10, 2021.

(51) Int. Cl.
*A61F 2/26* (2006.01)
*A61N 5/10* (2006.01)

(52) U.S. Cl.
CPC ...... *A61N 5/1002* (2013.01); *A61N 2005/1003* (2013.01); *A61N 2005/1019* (2013.01)

(58) Field of Classification Search
CPC ....... A61N 5/10; A61N 5/1001; A61N 5/1002; A61N 5/1014; A61N 5/1015; A61N 5/1027; A61N 2005/1003; A61N 2005/1004; A61N 2005/1005
See application file for complete search history.

(56) References Cited

U.S. PATENT DOCUMENTS

| | | | | |
|---|---|---|---|---|
| 4,763,642 | A * | 8/1988 | Horowitz | A61N 5/1014 600/7 |
| 5,429,582 | A * | 7/1995 | Williams | A61N 7/02 607/3 |
| 5,616,114 | A * | 4/1997 | Thornton et al. | A61N 5/1002 600/3 |
| 2007/0016179 | A1* | 1/2007 | Francescatti et al. | A61B 90/04 606/33 |
| 2015/0297763 | A1* | 10/2015 | Sutermeister et al. | A61M 37/00 424/1.61 |

OTHER PUBLICATIONS

Won Bae Han, et al. "Materials and Fabrication Strategies for Biocompatible and Biodegradable Conductive Polymer Composite toward Bio-Integrated Electronic Systems," Advanced Sustainable Systems/Early View/2100075, May 13, 2021, https://doi,org/10.1002/afsu.202100075, on line library.wiley.com, 1 page.

* cited by examiner

*Primary Examiner* — Samuel G Gilbert
(74) *Attorney, Agent, or Firm* — CHERSKOV FLAYNIK & GURDA, LLC (57) ABSTRACT

The invention provides a device for treating tumors at a target site, the device having a first balloon containing a radio isotope; a second balloon encasing the first balloon wherein the second balloon includes structures to create a void between the first balloon and the second balloon; and a third balloon encasing the second balloon, wherein the third balloon facilitates removal of material from the target site. The invention also provides a method for treating a tumor excise site, the method simultaneously exposing the tumor to heat and radiation.

8 Claims, 3 Drawing Sheets

HYPERTHERMIA BRACHYTHERAPY DEVICE AND METHOD FOR TREATING TUMORS

PRIORITY INFORMATION

This Utility Patent Application claims the benefits of U.S. Provisional Pat. Application number 63/243,092, filed on Sep. 10, 2021, the entirety of which is incorporated herein by reference.

BACKGROUND OF THE INVENTION

1. Field of the Invention

This invention relates to brachytherapy and more specifically, this invention relates to a device and method for optimizing radioisotope dose distributions and heat for in vivo treatment of tumors.

2. Background of the Invention

Treatment of some tumors has not significantly changed in the past 30 years. Generally, resection is made, and then followed up with radiation and/or chemotherapy, the former via brachytherapy which is insertion of a radioactive stent at or proximal to the resection site.

However, many aggressive neoplasms remain intractable. These neoplasms may manifest as defects, tumors (e.g. glioblastomas), or other intracranial/extra cranial maladies such as meningiomas, and gliomas. In situ bladder tumors and selective resected metastasis have a high chance of recurrence and may similarly benefit from brachytherapy.

Glioblastoma is a common, aggressive, treatment-refractory brain tumor causing a startling 3-4 percent of all cancer deaths. Life expectancy after initial diagnosis is short and on the order of 15 months.

Despite best available treatments such as radiotherapy, surgical resection, and chemotherapy, Glioblastoma remains, for the most part, an incurable disease. Patients typically succumb to recurrence at the original tumor site, despite adequate resections. The distinction between recurrence and persistence is clinical as subclinical tumors may persist despite aggressive imaging and local therapy.

Recurrence/persistence of glioblastomas is one of the most difficult challenges faced by clinicians. This is because of limited treatment tolerance of various structures. Generally, there is a lack of effective and tolerable treatments available for glioblastomas, and this demonstrates the critical need for innovative, novel treatment strategies.

Radiotherapy (including brachytherapy, stereotactic radiation, intensity modulated radiotherapy, neutron- and other-particle teletherapy) is also far from curative in glioblastoma multiformes (GBMs) and can only reduce the tumor burden within the brain to slow the disease process. In fact, 80 percent of tumors recur regardless of treatment, and within the original tumor location.

Radiation dose decreases exponentially from close to the source out to the treatment site. For example, the dose ratio in esophageal stents can decrease by a factor of 3 to 4 from superficial $D_{MAX}$ out to 0.5 centimeters. From 0.5 centimeters to 1 centimeter, the dose again decreases but by a lower factor. This is known as a decrease in the dose gradient. In typical brachytherapy applications, the dose at the surface of say a 4 centimeter sphere has a rapid fall off at diameter 5 cm. So, by adding a second void or balloon with a diameter of 5 cm, the dose decrement or the dose gradient is reduced.

Non-invasive brachytherapy is limited by the typical large radiation dose gradient from the dose closest to the sources and an effective and/or treatment depth which is often 0.5 cm (but may need to be deeper). As an example, the simple addition of a 0.5 cm spacer between the superficial dose ($D_{MAX}$) and a 0.5 cm prescription point changed from 2.24 to 1.67 per Mark Rivard Monte Carlo calculations of a 4 cm gliaSite spheroid. In many circumstances this dose gradient is related to toxicity. A situation in which there is no dose gradient would involve invasively placing sources within the treatment volumes, but this may impact critical structures.

As to brain maladies, the radiation field remains restricted in dose and/or in volume as there are critical structures (e.g. the brain stem, the optic tracts, the hippocampus speech center, etc.) which are extra sensitive to radiation exposure. For example, studies have demonstrated no survival improvement with whole-brain radiotherapy in this clinical situation. Rather, a higher incidence of treatment-induced brain injury occurs compared with regionally applied radiation, as evidenced by cognitive impairment.

Chemo-radiotherapy has been extensively utilized as a first-line treatment for post resection glioblastoma patients in combination with radiation therapy. (Temodar® and PCV chemotherapy have provided some improvement in survival rates.)

Altogether, despite multiple treatment approaches attempts and a longstanding field of research, glioblastoma patients still have one of the most dismal survival rates and urgently require an alternative solution to prolong survival and quality of life. A major challenge in developing effective therapies for glioblastoma is the tumor location: the human brain.

Past efforts (e.g., U.S. Pat. 4,763,671) for treating tumors included using catheters to deliver high frequency power, externally applied hyperthermia and radiation into a tumor site. But these techniques fall short of treating the excised tumor site in a form fitting manner, and so risk not exposing all aspects and remnants of a tumor mass.

Other efforts (U.S. Pat. 5,364,336) utilized microwave antennas for delivering heat and radiation to tissue. But these systems are not in vivo in design, not portable, and limited in time of application.

Neither of the two aforementioned patents are optimal modalities for radiation dose delivery or for thermal treatment.

A need exists in the art for a system and method for treating glioblastoma that demonstrate a benefit greater than the risk of damaging brain tissue. Radiation with hyperthermia, for example, could be administered within a range to sterilize the tumor tissue without causing toxic damage to the surrounding normal tissue, heretofore a greatly limiting factor. The effectiveness of the radiation could be supplemented with a second or third treatment modality (e.g., hyperthermia, chemotherapy, immunotherapy) but without causing unacceptable toxicity to the brain during treatment.

SUMMARY OF INVENTION

An object of the invention is to provide a system and method for treating post resection tumor sites that overcomes many of the drawbacks of the prior art.

Another object of the invention is to simultaneously enhance the efficacy of radiation and hyperthermia when treating illness. A feature of the invention is the utilization of a plurality of voids (wherein a brachytherapy vehicle incorporates a first void) to improve the depth dose delivered. (Depth dose is the ratio of the dose at the radiation source to the dose at the prescription point.) Given the low energies (e.g., less than or equal to 100 keV, and typically between about 20 and 100 keV) utilized in the invented treatment, the tissue $D_{MAX}$ dose is very high. An advantage of the invention is that the imposition of such voids reduces the slope of the dose decrement. Inasmuch as potential toxicities are influenced by treatment doses, the homogeneity due to the increased volume of void-containing delivery vehicles within a tumor site provided by the invention enhances tolerable tumor response.

Yet another object of the invention is to provide a system and method for treating glioblastoma and other spheroidal sites. A feature of the invention is utilization of brachytherapy and heat, both of which may be simultaneously applied in vivo. An advantage of the invention is that radiation dose rates and doses are kept below toxic thresholds but with a concomitant increase in survival rates.

Still another object of the invention is to provide a method for treating glioblastoma. A feature of the invention is the in vivo combination of brachytherapy and heat (in a range from 35-45° C., and preferably from 38-42° C.). An advantage of the invention is that it provides improved local control with reasonable tolerance. This is unexpected in glioblastoma treatment protocols inasmuch as that malady most frequently recurs or persists at the location of the original tumor. The advantage of the invention is that brachytherapy in combination with heat treatment within a patient has a geographic dose delivery advantage, which both limits radiation exposure to non-involved parenchyma while improving patient response.

Yet another object of the present invention is to provide an intrinsic compact device for treating glioblastoma. A feature of the device is that it molds itself to the targeted tissue, commonly the post resection surgical site. An advantage of the invention is that it provides radiation treatment, hyperthermia treatment, and waste/fluid removal simultaneously from a target site. The invention's utilization of very low energy and dose rates enables outpatient treatment delivery. Although applications using higher energy sources are possible, radiation safety considerations exist with those high energy usages.

Still another object of the present invention is optimize dose delivery to a tumor site. A feature of the invention is delivering radiation and heat simultaneously but within separate, dedicated void spaces. An advantage of the invention is that the voids define "spacers" to optimize radiation dose delivery while remediating (or even eliminating) confounding post-surgical fluid collections, and also enabling the addition of other treatment modalities such as diffusible medications, nanoparticles, and other vehicles.

Briefly, the invention provides a device for treating tumors at a target site, the device comprising a first balloon containing a radio isotope; a second balloon encasing the first balloon wherein the surface of the second balloon supports structures to create a void or space between the first balloon and the second balloon; and an optional third balloon encasing the second balloon, wherein the third balloon facilitates removal of material from the target site. Fewer or more balloons may be employed. For example, the second balloon may be utilized as a waste removal vehicle, thereby eliminating the need for a third balloon. By reversing the pressure gradient in the outer void (i.e., the space between the exterior surface of the second balloon and the patient) nanoparticles and/or medication can be diffused through the tissues. Alternatively, a fourth balloon may be utilized wherein it's outer surface (i.e., its parenchyma-contacting surface) supports additional medicaments in the form of nanoparticles, slow releasing healing agents, or other substances. A feedback mechanism (e.g., a thermocouple) to control the hyperthermia and accommodate homogeneity of the heat application is positioned within the void defined by the last balloon utilized and the tissue defining the resection site.

Specifically, the invention provides a system for treating tumors, the system comprising a first balloon adapted to receive radioactive isotope; a second balloon encapsulating the first balloon; and a third balloon encapsulating the second balloon wherein a space exists between the first balloon and the third balloon. The outer or third balloon may be similar to a polymer constructed surgical drain, such that a distal end of its drain conduit terminates either sub-galeal or in a reservoir located outside of the patient. ("Galeal" designates the connective tissue between the scalp and skull.) The middle balloon may act as a spacer or radiation and thermal insulating layer disposed between the radioisotope contained in the inner or core balloon and the patient so as to provide homogeneity of both the radiation dose and heat. This will protect or otherwise compensate for natural heat sinks in the body such as adjacent, un-diseased vasculature. This second balloon may contain a wire framework (for example comprised of Nitinol) adapted to accept and store heat generated by the radioisotope or otherwise supplied external of the patient. The second balloon (and its reversibly closable means of ingress/egress) may also accommodate any electronic device envisioned for use in this method, the electronic device including a thermocouple, dosimeter, heating element, etc. A third balloon, encapsulating the second balloon, may define a drain to either allow detritus to enter it, or to allow excess fluid to exit from it, particularly in situations where reverse pressure is utilized to infuse surround tissue with medicament contained by the third balloon.

In summary of this point, the space or void in the second balloon allows the depth dose to flatten out or otherwise decrease by a significant factor (e.g., between 1 and 3) in the case of glioblastoma stents. This provides a means for minimizing the dose at the surface of the delivery vehicle.

The invention also provides an in vivo method for treating glioblastoma at a target site, the method comprising concomitantly contacting the target site with radiation and heat; wherein the contacting step further comprises molding a radiation and heat emanating surface to the target site; and removing debris from the target site. The application of both radiation and heat may occur simultaneously, or with heat being added after radiation dosage, or vice versa which is to say heat added first, followed by radiation application.

BRIEF DESCRIPTION OF DRAWING

The invention together with the above and other objects and advantages will be best understood from the following detailed description of the preferred embodiment of the invention shown in the accompanying drawings, wherein.

DETAILED DESCRIPTION OF THE INVENTION

The foregoing summary, as well as the following detailed description of certain embodiments of the present invention, will be better understood when read in conjunction with the appended drawings.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

The following detailed description should be read with reference to the drawings in which similar elements in different drawings are numbered the same. The drawings, which are not necessarily to scale, depict illustrative embodiments and are not intended to limit the scope of the invention.

As used herein, an element or step recited in the singular and preceded with the word "a" or "an" should be understood as not excluding plural said elements or steps, unless such exclusion is explicitly stated. As used in this specification and the appended claims, the term "or" is generally employed in its sense including "and/or" unless the content clearly dictates otherwise.

Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

This invention is designed to treat tumor sites, post resection, and also to treat the resulting surgical cavities. Many surgical defects are spheroidal (i.e., hollow), rectangular, cuboidal, or combinations thereof such that non-spheroidal sites need to be accommodated. There are situations in which the organ at risk has a natural cavity e.g. urinary bladder and gall bladder in which the invention can be utilized The invention provides a method and system for simultaneously applying brachytherapy and heat in a synergistic approach to control Glioblastoma. The radiation and controlled heat is delivered safely and simultaneously to the tumor resection cavity. The invention enables the application of continuous lower dose rate brachytherapy with continuous non-fractionated hyperthermia, better feedback control of local hyperthermia, removal of unplanned fluids displacement between the device(s) and tissues and infusion injections of various chemotherapy substances, nanoparticles, or medicaments.

Figure 1:
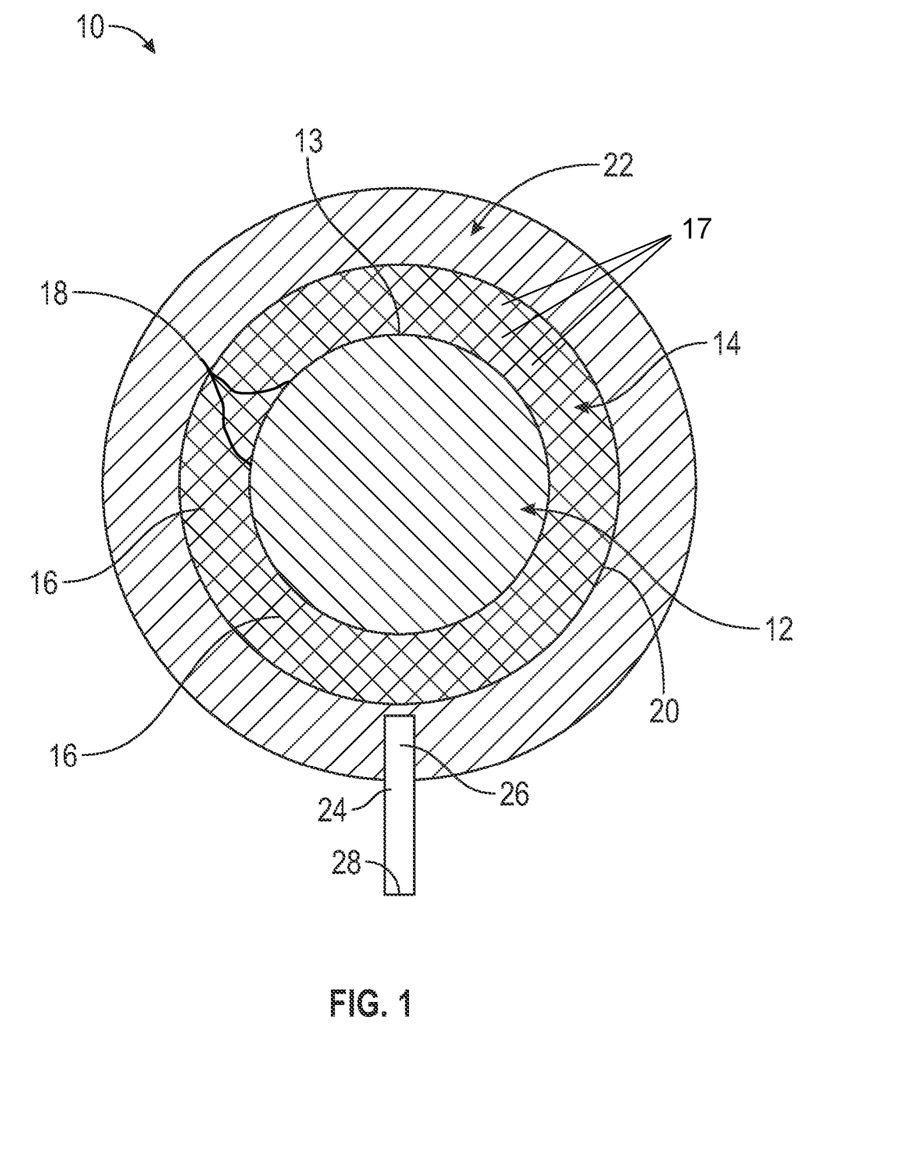
FIG. 1 is a schematic elevational view of a three balloon configuration for in vivo treatment of spheroidal tumors such as glioblastoma, in accordance with features of the present invention.

As depicted in FIG. 1, the invented device (designated as numeral 10) is a nested multi-balloon design, wherein each balloon is intended for specific applications to meet various treatment challenges. FIG. 1 features three balloons, but fewer or more balloons may be used, depending on the treatment sought, the radioisotopes used, and the amount of heat desired to be distributed. (For example, a two balloon system may be utilized.)

The innermost balloon 12 is adapted to contain the radio isotope or a plurality of radio isotopes. To aid in the pliability of the overall construct, the radioisotope(s) may be contained within a liquid carrier so as to be a solute in a solvent contained by the first or innermost balloon. Alternatively, the radioisotope itself may be of a liquid phase. Inasmuch as there is no perfect or standard radioisotope, the device is compatible with a variety of radioisotope options, thereby allowing the physician to select the most optimal radio isotope for each individual patient.

In an embodiment of the invention, the first balloon defines a single void or space (e.g., sans any internal partitions or barriers which would otherwise form sub spaces) such that the radioisotope is free flowing throughout the entire void. The isotope may be inserted via syringe through a skirt (i.e., the neck) of the balloon. Alternatively, the balloon maybe immersed within a solution containing the radioisotope and allowed to expand, after which the skirt or neck is tied off, melted closed, or sealed closed via adhesive.

Other means of ingress/egress may be utilized. For example, the balloon may be integrally molded with a septum to allow deflated transport to the surgical facility; the balloon being inflated by the surgeon via syringe whereby the needle of the syringe reversibly breaches the septum barrier. This syringe approach will allow the balloon to be inflated in a bespoke fashion after the surgeon determines the metes and bounds of the resection site. The septum is designed to prevent leakage of the fluid isotope from the first balloon.

Alternatively, or in combination with the above closing means, the balloon containing the isotope may further comprise a valve (element 17, FIG. 3) which may be reversibly opened or closed.

The radioactive isotope is a medical isotope selected from the group consisting of cesium-133, iodine 125, samarium (e.g., Sm153), ytterbium (e.g., Yb169), palladium (e.g., Pd103), iridium (e.g., Ir192) and combinations thereof, and other radio isotopes. The radiation strength is selected to deliver either low dose radiation (LDR) or very low dose radiation (VLDR) brachytherapy over a finite period of time. The implant may be permanent or semi-permanent. As such, dosages provided by the radioisotopes typically may be between 20 grays (Gy) and 100 Gy. Preferably, the ratio of $D_{MAX}$ and depth dose is less than 2, which means that the radiation dose at the radiation source does not decrease by more than half at the eventual treatment site. This will minimize any hot spots which therefor will decrease the risk of radio necrosis, ulcerations, fistulas, etc. Thus, good tolerance is conferred.

A secondary spacer balloon 14 encapsulates or otherwise contains the inner balloon 12. This spacer balloon has a diameter sufficient to improve depth dose characteristics (e.g., a diameter ranging from 0.25 to 0.75 cm and preferably 0.5 cm.) The inner balloon (aka a brachytherapy "stent") will be monitored to ensure leak-proof containment of radioactive solution. Monte Carlo calculations, which defines a well-established class of computational algorithm, will be performed to assess radiation depth, homogeneity of distribution, and maximal doses. The ratio of maximum dose (Dmax) to depth should be less than 2, which should provide good tolerance against over exposure to radiation and heat.

The second balloon defines a scaffold 16 (e.g. a webbing, net, or grid), which may be rigid, semi-rigid, or flexible. (In an embodiment, the device would conform to the shape of the surgical defect or organ volume, such as the bladder.) The scaffold may define a porous structure capable of absorbing and perhaps homogenizing the heat, medicament or any other fluid substance in physical contact with the porous structure. Alternatively, the scaffold may define an adsorbent so as to adsorb materials for later distribution during treatment, depending on pH, temperature, solubilities, emf exposure, etc., per treatment protocols.

Another alternative is the scaffold defining an innermost surface 18 contacting the first balloon 12, and a radially displaced surface contacting the third balloon 22. Radially extending struts 21 may be provided to maintain the space defined by the innermost surface 18 and outer-most radially displaced surface 20 of the scaffold such that no other structures aside from the struts exist between an exterior surface 13 of the first balloon and the third balloon.

Instead of struts, the scaffold may comprise a second balloon to maintain the distance between the first balloon and the second balloon.

Generally, the scaffold has a first surface 18 contacting the exterior surface 13 of the first balloon 12. The scaffolding 16 creates a space 17 or plurality of spaces (e.g. a void or plurality of voids) for dissipation of heat generated by the radioisotopes, or of the heat supplied from outside the body.

A purpose of the scaffolding is to provide space (e.g., approximately 0.2 to 0.7 cm, and preferably 0.5 cm) to allow the depth dose curve to flatten and potentially as a means to produce the hyperthermia. The nitinol framework can generate heat by electrical charging, stressing, for example by phase conversion of austenite to martensite (as discussed infra), and similar phase changes exhibited in other metals. For example, nitinol can be heated with an in vitro or in vivo DC power source to a temperature of between 35° C. and 45° C.

The scaffolding creates a void or voids that is/are radially displaced from the internal void defined by the first balloon 12. Heat generation and transfer to target sites radially displaced from a second exterior surface 20 of the second balloon is thus more effective within the spacer balloon rather than within the larger inner balloon.

Figure 3:
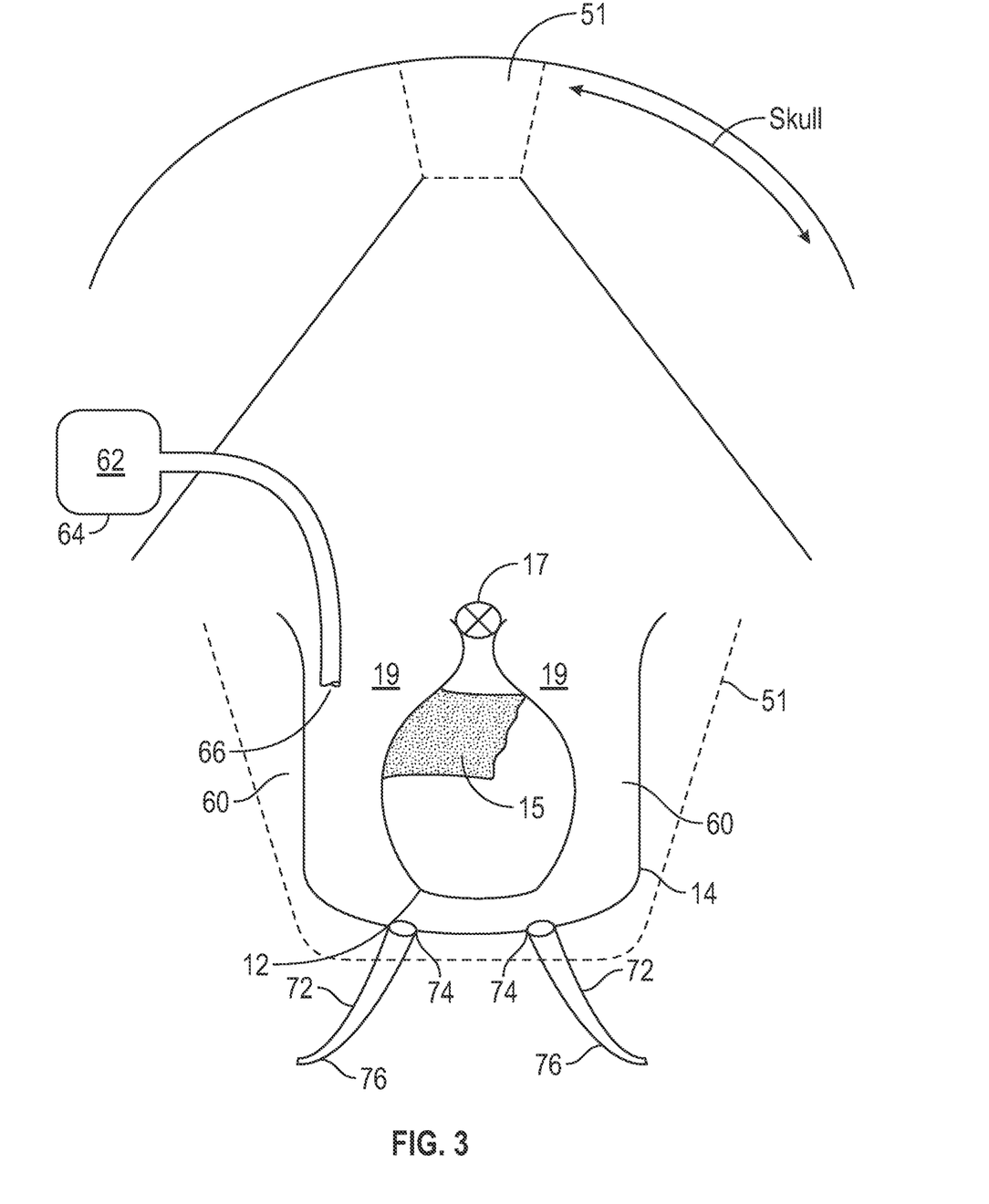
FIG. 3 is a schematic diagram of an implanted device in the skull of a patient, in accordance with features of the present invention.

In an embodiment of the invention, the scaffold is in thermal communication with the first balloon. The scaffold extends from the first balloon to the third balloon. The scaffold may be a thermally conductive material selected from the group consisting of nitinol or similar metals. Notwithstanding the foregoing, an embodiment of the invention is depicted in FIG. 3 which does not feature the scaffolding, rather, just a space 19 defined by the exterior surface of the first balloon 12 and an interior surface of the second balloon 14.

An outermost balloon 22, encapsulating the second balloon, provides a second void to facilitate drainage of potentially intervening fluids, blood, and other debris and is also utilized to provide local medications, nanoparticles, or other desired substances to the surface tissue. This second void may be utilized to remove post-surgical fluids. This second void may also be used to reverse the pressure gradient imposed by some medications, nanoparticles and other locally applied immunotherapies. Such a reversal provides a means for diffusing of some the aforementioned medications, nanoparticles and other substances. For example, pressure within the second void could be reversed to "insert" nanoparticles, immunotherapy and chemotherapy. The nanoparticles (such as Ferro-magnetic particles) may be activated via ultrasound, radiofrequency or the aforementioned heat application to provide a third treatment modality.

One means for providing drainage from the excise site, or medicament delivery to the excise site is a conduit 24. The conduit 24 terminates in vivo, at a first end 26 at the excise site and at a second end 28 remote from the excise site (e.g., sub-galeal, subcutaneously and/or just overlying the scalp) or perhaps outside the body of the patient.

In an embodiment of the invention, the third balloon defines an exterior surface and the exterior surface conforms to an excision site of the tumor.

The second void also provides a further means for dose decrement. Dose decrement is due both to the geometry and attenuation from whatever material is within the second (or middle) void.

A unique feature of the invention is distributing heat evenly, or selectively, to a target site. (In the case of selective heat application, localization of heat would be controlled by an electrical feed-back mechanism enabled by the aforementioned thermocouples or sensors.) The invented device manipulates undesirable cold/hot spots by changing the local thickness from which fluid within the spacer balloon circulates or manipulating locally applied electrical current. Activating or otherwise circulating the fluid(s) provide a means for homogenizing the heat application. Another temperature varying means is directing warmer or cooler fluids where needed based on information provided by various temperature probe-based feedback mechanisms. In addition, the clinician may desire that part of the appliance deliver more radiation and/or heat in a certain direction, and our design offers that capability.

Salient features of the invented design include the following:
It is adaptable to the irregularly-shaped surgical cavity to increase uniformity of treatment delivery;
It is compatible with multiple radio-isotopic solutions, particles and other vehicles, thereby allowing physicians to select the vehicles based on clinical criteria;
It is equipped with continuous temperature monitoring, allowing an opportunity for real-time adjustment of fluid delivery to ensure most effective treatment while remaining in tolerable range.

An alternative to the middle balloon (or in addition to the middle balloon) is inclusion of high atomic material (e.g., high barn substances) within the radioisotope solution contained in the first balloon. This provides self-filtration of the radioisotope to remove low energy emanations. For example, the incorporation of high atomic number material in either the inner balloon void or the second solution is intended to relatively decrease the superficial radiation dose by absorbing relatively low radiations (e.g., less than 20 keV photons).

Brachytherapy Detail

Optimal potential treatment volumes embody different geometries depending on the resection site and therefore may not include a true sphere. The inventors addressed this issue below by using liquid isotope and spacer between the inner and middle balloons that may contain a form fitting mesh e.g. nitinol or other materials. The nitinol offers fatigue resistance with potential for outward radial pressure. Optionally, a pressure gradient could be utilized to help remove any post-operative interstitial fluid between the middle and outer most balloons and tissues; the gradient could be reversed if one wanted to diffuse medications nanoparticles etc. As such, the applied pressure resulting in the gradient may be either negative or positive, relative to the ambient pressure of the resected region, depending on whether positive or negative pressure is to be applied to the region.

There is some advantage to use a central source as the dose gradient defined as the maximal radiation dose closest to the sources and a prescription depth often 0.5 cm relatively improves as the source is further displaced from the target. This is the most common situation for HDR brachytherapy. The disadvantage is that it is a short linear source and the treatment target is at best spheroidal. HDR requires fractionation which is a compromise when compared to LDR brachytherapy, currently the standard of care. LDR sources (e.g., Iridium 192) have a more limited availability. Continuous low dose or very low dose radiation also have a theoretical biological advantage with higher Linear Energy Transfer. The risk of radiation unwanted exposure and leakage is being addressed including chelation of the sources to expedite excretion.

The liquid isotope would further improve the homogeneity of the radiation source(s) comparing almost infinite sources to fewer point sources could improve the dose gradients. The disadvantage of most liquid sources is the absence of an absorber of the undesirable lower energy radiation emanations. The addition of high Z material (discussed infra) to the radio isotopic solution or even incorporated into the balloon wall is a means to solve this issue.

The invented devices allow the use of HDR, LDR, or vLDR brachytherapy. In the brain, the standard of care is to limit the presence of a foreign body. This translates to limiting application to a few days (e.g., 3-5 days) unless in vivo studies determine that this issue is not a limitation.

vLDR has a higher linear energy transfer (LET) and lower oxygen enhancement ratio (OER) which may translate to a better radio-biological response. The use of an isotope such as Sm 153 with a short half-life of less than two days is a compromise. The challenge is that it produces 71 percent beta (500-900 KEV) inasmuch much as a preferred objective is to minimize the Beta particles. Incidentally this is the same percentage of the earth covered by water. Whereas the use of an isotope with a longer half-life (such as I125, at 59.5 days) may be more practical for an implant that would be used for a short time, the use of very low energies allows patients to be treated in a non-shielded room and even be in the public with reasonable restrictions.

The advantage of a liquid source is that the fluid will fill the space within certain limits. A central source is attractive as in HDR but should be spherical and would require a facility shielded room fractionation etc. Theoretically continuous radiation which had evolved over nearly a century which has an advantage, but may present a radio protection issue. In contrast, vLDR brachytherapy may offer treatment with better radiation exposure to others. Thermodynamics suggest that the temperature of two masses physically intertwined would equilibrate. Naively extrapolating the tissue surrounding a 5 cm diameter warm spheroid would have a modest temperature increase modified by heat sinks and other heat attenuation phenomena.

Hyperthermia Detail

Presently hyperthermia is usually delivered by external applicators which of necessity is fractionated. We are addressing this problem by incorporating a means of hyperthermia generation. There are numerous local means to deliver the hyperthermia; as for example, by using a proposed nitinol mesh with electrical stimulation with feedback control. This requires a square wave DC source. Other means of generation of hyperthermia from nitinol include state change from austenite to martensite, and stress. Other hyperthermia sources generated externally may also be attractive. Microcomputer controlled feedback could be developed which was an obstacle in the past. A new modality; that is, concomitant continuous radiation and hyperthermia now becomes feasible is potentially available as an outpatient.

Electrical induced local heating could include a feedback mechanism. Other advantages include biocompatibility, production of radial pressure and fatigue resistance. Other nitinol based means to produce hyperthermia include stress and conversion austenite to martinet.

The aforementioned possible theoretical third balloon offers the opportunity to remove any intervening fluid between the device and tissue. It offers the opportunity to deliver a variety of medications, nanoparticles etc.

Figure 2:
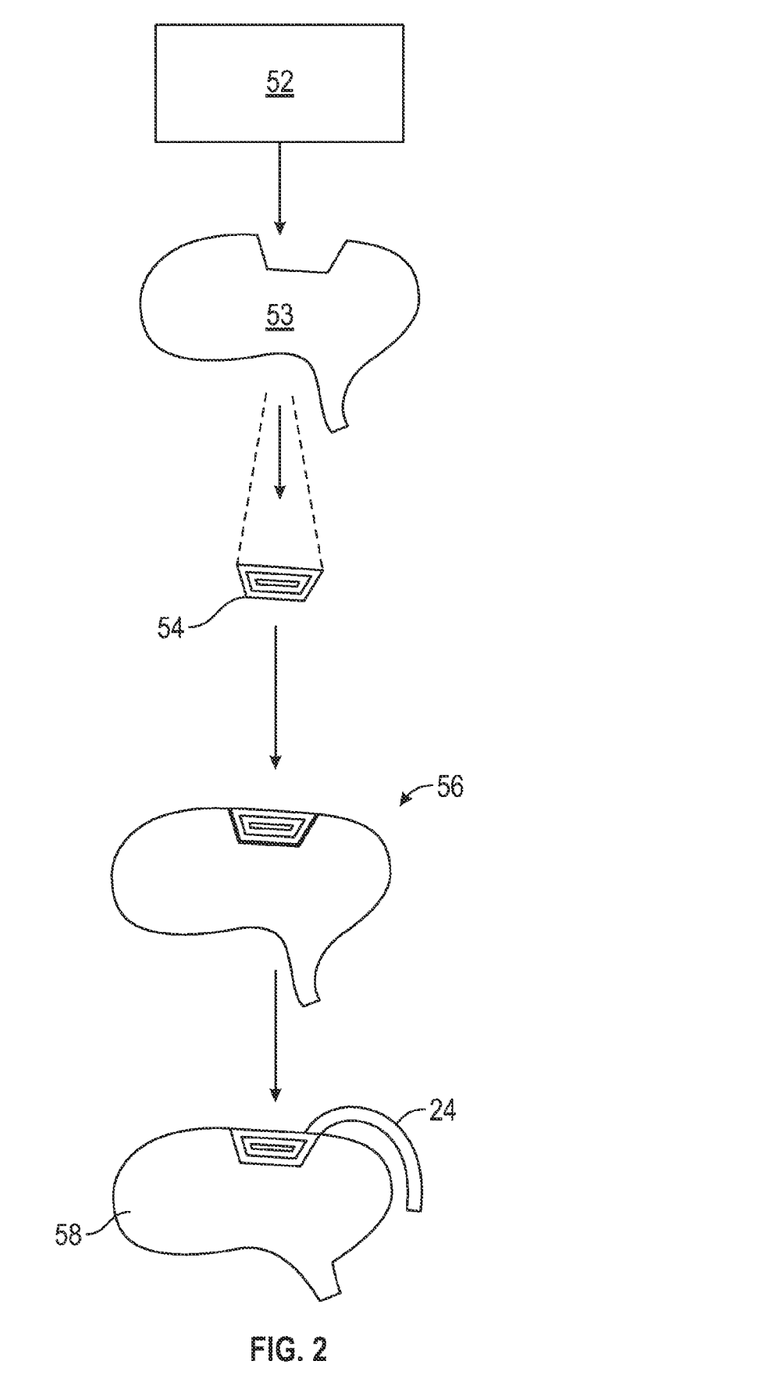
FIG. 2 is a flow chart of procedures associated with the invented method for treating glioblastoma, in accordance with features of the present invention.

FIG. 2 is a schematic depiction of the method for treating an excised tumor site. The method is designated generally as numeral 50. A first step 52 is an evaluation of the excised site 51, in terms of its location in the body (e.g., in instances of glioblastoma, the brain 53 would be the location). The site is evaluated for its width, depth, associated vasculature, and possible drainage routes for post-operative detritus. Assembly 54 of the afore-described construct is determined based on this situs evaluation. This assembly includes selection of radio-isotope to be contained in the center or innermost balloon 12, size of scaffolding 16 encircling the innermost balloon, and the size of the outermost balloon.

The bespoke construct is then placed 56 into the excise site, and the site closed via standard surgical closure techniques including suturing 58. Optionally, provisions are made for a drainage conduit, as also described supra.

Treatment includes simultaneous application of heat and radiation to the now closed excised site. Application of heat may be delayed until initial radiation treatment has begun.

FIG. 3 is a schematic diagram of the invented device implanted within the excised site 51 or surgical resection defect described in FIG. 2, supra. The figure shows the site 51 filled with a 2-balloon embodiment, the inner balloon 12 encapsulated by the second balloon 14. The voids space 19 as described supra, is shown between the first balloon 12 and second balloon. This space 19 is approximately 0.5 cm (e.g., between 0.3 and 0.7 cm) between the surfaces of the first and second balloon.

FIG. 3 also shows a means for compressing fluid residing between the exterior surface of the second (in this embodiment, the outer-most) balloon 14 and inwardly facing surfaces of the resection site, those two surfaces defining an outer void 60. One compression means is a bulb 62 positioned either external of the body, or subcutaneously to allow patient actuation. The compression bulb 62 defines a first proximal end 64 for patient actuation and a distal end 66 which is in fluid communication with the outer void 60. In this arrangement, the outer void 6 defines a compression chamber to provide fluid drainage and access to medications via imposition of a pressure gradient, as discussed supra.

The outer void is also adapted to receive electronic probes for biofeedback, such as temperature and pressure monitoring, and dosimetry measurements.

Also, the outer void 19 may be populated with silicon conduits 72, the ends of those conduits having regions forming apertures, reminiscent of surgical drains. Each of the conduits would have a first end 74 forming the apertures residing within the void, and a second 76 end residing outside of the resected area 51. The apertures may be gauged to accommodate the positive or negative pressures imposed within the resected region, those pressures discussed supra.

It should be appreciated that this two balloon arrangement is not relegated solely to the brain venue, but can also be applied to nasal cavity and nasopharynx venues, the gall bladder, urinary bladder, the ovaries, uterus, vagina, metastasis associated with the liver, and other regions.

Separately, the inner balloon of the embodiment shown in FIG. 3 may also be partially overlaid with a foil 15 so as to prevent undesirable radiation exposure where not needed. The foil may be applied to any region of the balloon, for example its neck or collar, its base, its midsection, or a combination of these positions.

Heat Source Detail

Various means for producing heat may be utilized, for example circulating warmed fluids from outside the patient's body to the tumor site. Other heating means include subjecting the nitinol structure to DC current for a time sufficient to heat the structure to the desired temperature. Direct heating of the nitinol is more controllable. Whichever heat source is utilized, a feedback mechanism can be used to regulate the heat generation and its distribution.

Encapsulation: To protect the patient from moving components, the entire heat pump may be encapsulated. A thermally conductive polymer will be used to encapsulate the heating end to ensure maximum heat transfer. The remainder of the system is encapsulated in a catheter system.

Increasing the latent heat of transformation will reduce the speed necessary to reach the desired effect, thereby increasing the device safety profile.

The goal is to maintain temperature within 0.1° C. over various periods of time. In an embodiment of the invention, the optimal temperature is empirically (e.g., though modeling) or experimentally defined (e.g., via MRI) for various sites for the brain. Generally any temperature would be maintained at or less than 42° C. over a period of time which is again determined empirically or experimentally to effect therapeutic value without damage to surrounding parenchyma. This system also allows for control over increasing or decreasing temperature on a rapid time-scale to adapt the hyperthermia aspect of the treatment method in response to treatment needs.

Example

The invention provides a method and system for administering moderate hyperthermia (up to about 42° C.) and low-dose rate (LDR), very low dose rate (VLDR) or high dose rate (HDR) brachytherapy in the brain following surgical resection of a primary tumor. This thermo-brachytherapy combination not only creates a novel treatment option for patients, but also may improve glioblastoma prognosis and increase the aforementioned patient survival rates with reasonable tolerance -- a goal that has never before been successfully achieved by any significant margin in this field.

The invention provides a method and system for administering moderate hyperthermia (up to about 42° C.) and low-dose rate (LDR), very low dose rate (VLDR) or high dose rate (HDR) brachytherapy in the brain following surgical resection of a primary tumor. This thermo-brachytherapy combination not only creates a novel treatment option for patients, but also may improve glioblastoma prognosis and increase the aforementioned patient survival rates with reasonable tolerance -- a goal that has never before been successfully achieved by any significant margin in this field.

An embodiment of the invented system comprises an inner balloon made of biocompatible polymers. These biocompatible substrates may be thermally conductive organic and inorganic polymer material, such as cellulose nanofibers, (e.g., nanofiber/hydroxylated boron nitride nanosheet film), poly butylene succinate nano-composites, and combinations thereof. The inner balloon will have variable dimensions depending on the receiving surgical cavity. It is leak-proof to contain radio-isotopic solution.

The scaffold or lattice work and the middle balloon is comprised of polymer similar to that of the inner balloon, and nitinol material. The polymer may include a silicone-bismuth film adhering to its exterior surface, wherein the silicone is used to further prevent leakage and the bismuth or some other high atomic number element is used as additional radiation shielding. Solutions containing high z elements (elements with relatively high numbers of protons in their nucleus, such as Ti, Cr, Al, Cu, V, Fe, Pb, etc.,) may be added to the radio isotope solution to minimize very low energy radiations. High atomic number (Z) materials used in various prostheses and Pb used for shielding electron beams produce dose perturbations. An accurate knowledge of dose perturbation and transmission through these materials is required for curative and re-irradiation planning which is not available for all clinical electron beams.

In an embodiment of the invention, the nitinol material may be a half centimeter thick or suitable thickness to maintain spacing between the innermost and middle balloon. This construct enabled effective containment of hyperthermic solutions.

The outer balloon will also comprise polymer material and define an inner void large enough to encompass or otherwise completely encapsulate the inner and middle balloons. This outer balloon is flexible enough to adapt to irregular cavity spaces. This outer balloon also has a means for draining post-surgical fluids via a surgical drain or conduit connected at its distal end (i.e. outside the patient) to a collapsed vacuum bulb or other negative pressure device.

Tables 1 and 2 provide simulation data comparing radiation doses at various depths over a span of 96 hours. Cesium 1-131 and Iodine 125 are the isotopes featured in the tables.

TABLE 1

Monte Carlo simulation comparing radiation dose from balloon surface for 50 Gy prescription dose to 5 mm depth

| Depth from Surface (mm) | 2 cm Balloon | | 4 cm Balloon | |
|---|---|---|---|---|
| | Cs-131, Gy | I-125 Gy | Cs-131, Gy | I-125, Gy |
| 0 | 154 | 160 | 107 | 112 |
| 2 | 88 | 90 | 74 | 76 |
| 4 | 50 | 60 | 56 | 57 |
| 6 | 43 | 42 | 45 | 44 |
| Activity (mCi) | 224 | 97 | 690 | 312 |

TABLE 2

Monte Carlo simulation comparing radiation dose from balloon surface for 60 Gy prescription dose to 10 mm depth

| Depth from Surface (mm) | 2 cm Balloon | | 4 cm Balloon | |
|---|---|---|---|---|
| | Cs-131, Gy | I-125 Gy | Cs-131. Gy | I-125. Gy |
| 0 | 487 | 397 | 284 | 232 |
| 2 | 279 | 223 | 197 | 158 |
| 4 | 188 | 148 | 150 | 119 |
| 6 | 135 | 105 | 119 | 92 |
| 8 | 102 | 78 | 96 | 74 |
| 10 | 60 | 60 | 60 | 60 |
| Activity (mCi) | 537 | 240 | 1387 | 649 |

It is to be understood that the above description is intended to be illustrative, and not restrictive. The above-described embodiments (and/or aspects thereof) may be used in combination with each other. In addition, many modifications may be made to adapt a particular situation or material to the teachings of the invention without departing from its scope. For example, nanoparticles medicaments can be diffused from the outer or third balloon possibly enhanced by positive osmotic or other pressure. Ferrous-based nanoparticles will emanate heat when subjected to radio frequencies, ultra sonic radiation or other means to provide supplemental hyperthermia. Also, an appropriate antenna constructed perhaps of nitinol may generate radio frequency, ultrasonic or other means can generate supplemental hyperthermia.

While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all sub-ratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The embodiment of the invention in which an exclusive property or privilege is claimed is defined as follows:

1. A system for treating tumors, the system comprising:
    a. a first leak proof balloon adapted to receive radioactive isotope;
    b. a second leak proof balloon encapsulating the first leak proof balloon so as to form a first space between the first leak proof balloon and the second leak proof balloon;
    c. a third balloon encapsulating the second leak proof balloon wherein a second space exists between the first leak proof balloon and the third balloon;
    wherein the second leak proof balloon defines a scaffold contacting an exterior surface of the first leak proof balloon to maintain a space between the first leak proof balloon and the third balloon.

2. The system as recited in claim 1 wherein the scaffold contacts the first leak proof balloon and the third balloon.

3. The system as recited in claim 1 wherein the scaffold is a thermally conductive material selected from the group consisting of nitinol, tin, steel, and combinations thereof.

4. The system as recited in claim 1 wherein the first leak proof balloon defines a single void and the radioisotope is free flowing within the void.

5. The system as recited in claim 1 wherein the radioactive isotope is a medical isotope selected from the group consisting of cesium-133, iodine 125, samarium, ytterbium, palladium, iridium, other isotopes, and combinations thereof.

6. The system as recited in claim 1 wherein the third balloon defines an exterior surface and the exterior surface is capable of conforming to an excision site of the tumor.

7. The system as recited in claim 1 wherein a radio-opaque substrate overlays a region the first leak proof balloon to prevent radiation exposure to healthy patient tissue proximal to the region.

8. The system as recited in claim 7 wherein the substrate is a malleable foil.

* * * * *